(12) United States Patent
Hoopes

(10) Patent No.: US 7,041,883 B2
(45) Date of Patent: May 9, 2006

(54) POTATO CULTIVAR FL 2048

(75) Inventor: Robert W. Hoopes, Rhinelander, WI (US)

(73) Assignee: Frito-Lay North America, Inc., Plano, TX (US)

( * ) Notice: Subject to any disclaimer, the term of this patent is extended or adjusted under 35 U.S.C. 154(b) by 0 days.

(21) Appl. No.: 10/896,479

(22) Filed: Jul. 21, 2004

(65) Prior Publication Data

US 2006/0021097 A1    Jan. 26, 2006

(51) Int. Cl.
| | |
|---|---|
| A01H 1/00 | (2006.01) |
| A01H 1/02 | (2006.01) |
| A01H 5/00 | (2006.01) |
| C12N 15/82 | (2006.01) |
| C12N 5/02 | (2006.01) |

(52) U.S. Cl. .................. 800/317.2; 800/260; 800/266; 800/278; 800/284; 800/298; 800/300; 800/301; 800/302; 435/429

(58) Field of Classification Search .............. 800/260, 800/263, 265, 266, 268, 269, 277, 278, 279, 800/284, 287, 317.2; 435/417, 418, 421, 435/429, 430, 430.1, 468, 469, 470
See application file for complete search history.

(56) References Cited

U.S. PATENT DOCUMENTS

| | | | | |
|---|---|---|---|---|
| 5,523,520 A | * | 6/1996 | Hunsperger et al. | ........ 800/260 |
| 6,100,456 A | * | 8/2000 | Sticklen et al. | .......... 800/317.2 |
| 6,492,580 B1 | * | 12/2002 | Hoopes | .................... 800/317.2 |

OTHER PUBLICATIONS

Kraft et al. 2000. Theor. Appl. Genet. 101: 323-326.*
Eshed et al. 1996. Genetics 143: 1807-1817.*
Visker et al. 2003. Theor. Appl. Genet. 106: 317-325.*
Darnell et al. 1990. Molecular Cell Biology, Scientific American Books, Inc. New York, New York, p. 478.*
Bennetzen, et al., 1992. Approaches and progress in the molecular cloning of plant disease resistance genes. *In* Genetic Engineering. 14:99-124.
Darnell, et al., 1990. DNA replication, repair and recombination. *In* Molecular Cell Biology, 2$^n$ Edition, W. H. Freeman and Company, p. 478.

DeBolle, et al., 1996. Antimicrobial peptides from *Mirabilis jalapa* and *Amaranthus caudatus*: expression, processing, localization and biological activity in transgenic tobacco. Plant Molecular Biology. 31:993-1008.
Eshed, et al., 1996. Less-than-additive epistatic interactions of quantitative trait loci in tomato. Genetics. 143:1807-1817.
Goth, et al., 1995. Relative resistance of the potato cultivar Krantz to common scab caused by *Streptomyces scabies* as determined by cluster analysis. American Potato Journal 72:505-511.
Hemmat, et al., 1998. Molecular markers for the scab resistance (V) region in apple. J. Amer. Soc. Hort. Sci. 123 (6):992-996.
Kraft, et al., 2000. Linkage disequilibrium and fingerprinting in sugar beet. Theor. Appl. Genet. 101:323-326.
Lopez, et al., 1987. Genotype x environment interactions, correlations and combining ability for six traits in potato. American Potato Journal. 64:447.
Mendiburu, et al., 1997. The significance of 2N gametes in potato breeding. Theor. Appl. Genet. 49:53-61.
Michelmore, et al., 1991 Identification of markers linked to disease-resistance genes by bulked segregant analysis: a rapid method to detect markers in specific genomic regions by using segregating populations. PNAS (USA) 88:9828-9832.
Pang, et al., 1992. Expression of a gene encoding a scorpion insectotoxin peptide in yeast, bacteria and plants. Gene 116:165-172.
Van Ooljen, et al., 1994. An RFLP linkage map of *Lycopersicon peruvianum*. Theor. Appl. Genet. 89:1007-1013.
Visker, et al., 2003. Can the QTL for late blight resistance on potato chromosome 5 be attributed to foliage maturity type? Theor. Appl. Genet. 106:317-325.

* cited by examiner

*Primary Examiner*—David H. Kruse
*Assistant Examiner*—Keith O. Robinson
(74) *Attorney, Agent, or Firm*—Jondle & Associates P.C.

(57) ABSTRACT

A novel potato cultivar of the genus and species *Solanum tuberosum*, designated FL 2048, is disclosed. The invention relates to the tubers of potato variety FL 2048, to the plants of potato variety FL 2048, to the seeds of potato variety and to methods for producing hybrid potato variety. The invention further relates to potato variety tubers, seeds and plants produced by crossing the potato variety FL 2048 with another potato plant, and to Single Gene Converted plants.

18 Claims, No Drawings

POTATO CULTIVAR FL 2048

BACKGROUND OF THE INVENTION

The present invention relates to a novel potato variety and to the tubers, plants, plant parts, tissue culture and seeds produced by that potato variety.

The publications and other materials used herein to illuminate the background of the invention and, in particular cases, to provide additional details respecting the practice, are incorporated by reference and for convenience, are referenced in the following text by author and date and are listed alphabetically by author in the appended bibliography.

The potato is the world's fourth most important food crop and by far the most important vegetable. Potatoes are currently grown commercially in nearly every state of the United States. Annual potato production exceeds 18 million tons in the United States and 300 million tons worldwide. The popularity of the potato derives mainly from its versatility and nutritional value. Potatoes can be used fresh, frozen or dried, or can be processed into flour, starch or alcohol. They contain complex carbohydrates and are rich in calcium, niacin and vitamin C.

To keep the potato industry growing to meet the needs of the consuming public, substantial research and development efforts are devoted to the modernization of planting and harvesting of fields and processing of potatoes, and to the development of economically advantageous potato varieties. Through crossbreeding of potatoes, researchers hope to obtain potatoes with the desirable characteristics of good processability, high solids content, high yield, resistance to diseases and pests and adaptability to various growing areas and conditions.

The U.S. acreage planted in potatoes has declined since the 1960s and 1970s, and this decline, coupled with increasing consumption, must be offset by higher useable yields. In some areas, diseases and pests damage crops despite the use of herbicides and pesticides. The problem of the golden nematode in the United States, presently endemic to portions of New York State, is one example of the destruction to susceptible potato varieties. Potato varieties with high yields, disease resistance and adaptability to new environments can eliminate many problems for the potato grower and provide more plentiful and economical products to the consumers.

For the potato chip processing industry, potatoes having high solids content, good shipping qualities and good finished chip color can increase production volumes and efficiencies and product acceptability. Potato varieties which yield low-solids tubers result in unnecessary energy usage during the frying process. Moreover, as solids content increases, the oil content of fried products decreases, which is a favorable improvement. Potato varieties in the warm southern tier of states are most in need of solids improvement overall, while those varieties grown and stored in the colder northern tier of states are most in need of the ability to recondition after cool or cold storage to increase their value for use in the potato chip industry. Reconditioning is necessary to elevate the temperature of the potatoes after cold storage and before further processing.

The research leading to potato varieties which combine the advantageous characteristics referred to above is largely empirical. This research requires large investments of time, manpower, and money. The development of a potato cultivar can often take up to eight years or more from greenhouse to commercial usage. Breeding begins with careful selection of superior parents to incorporate the most important characteristics into the progeny. Since all desired traits usually do not appear with just one cross, breeding must be cumulative.

Present breeding techniques continue with the controlled pollination of parental clones. Typically, pollen is collected in gelatin capsules for later use in pollinating the female parents. Hybrid seeds are sown in greenhouses, and tubers are harvested and retained from thousands of individual seedlings. The next year a single tuber from each resulting seedling is planted in the field, where extreme caution is exercised to avoid the spread of virus and diseases. From this first-year seedling crop, several "seed" tubers from each hybrid individual which survived the selection process are retained for the next year's planting. After the second year, samples are taken for density measurements and fry tests to determine the suitability of the tubers for commercial usage. Plants which have survived the selection process to this point are then planted at an expanded volume the third year for a more comprehensive series of fry tests and density determinations. At the fourth-year stage of development, surviving selections are subjected to field trials in several states to determine their adaptability to different growing conditions. Eventually, the varieties having superior qualities are transferred to other farms and the seed increased to commercial scale. Generally, by this time, eight or more years of planting, harvesting and testing have been invested in attempting to develop the new and improved potato cultivars.

Long-term, controlled-environment storage has been a feature of the northern, principal producing areas for many years. Potatoes harvested by October must be kept in good condition for up to eight months in temperatures that may drop to −30 degrees C. at times and with very low relative humidity in the outside air. Storages are well insulated, not only to prevent heat loss but also to prevent condensation on outside walls. The circulation of air at the required temperature and humidity is automatically controlled depending on the purpose for which the potatoes are being stored. Sprout inhibition is now largely carried out in storage as it has been found to be more satisfactory than the application of maleic hydrazide (MH30) in the field.

Proper testing of new plants should detect any major faults and establish the level of superiority or improvement over current varieties. In addition to showing superior performance, a new variety must be compatible with industry standards or create a new market. The introduction of a new variety will increase costs of the tuber propagator, the grower, processor and consumer; for special advertising and marketing, altered tuber propagation and new product utilization. The testing preceding release of a new variety should take into consideration research and development costs as well as technical superiority of the final variety. Once the varieties that give the best performance have been identified, the tuber can be propagated indefinitely as long as the homogeneity of the variety parent is maintained.

For tuber propagated varieties, it must be feasible to produce, store and process potatoes easily and economically.

Thus, there is a continuing need to develop potato cultivars which provide good processability out of storage, with minimal bruising, for manufacturers of potato chips and other potato products and to combine this characteristic with the properties of disease resistance, resistance to pests. The present invention addresses this need by providing the new variety as described herein.

SUMMARY OF THE INVENTION

According to the invention, there is provided a novel potato cultivar of the genus and species, *Solanum tuberosum*, designated FL 2048. This invention thus relates to the tubers of potato variety FL 2048, the plants and plant parts of potato variety FL 2048 and to methods for producing a potato plant produced by crossing the potato variety FL 2048 with itself or another potato variety. This invention further relates to hybrid potato seeds and plants produced by crossing the potato variety FL 2048 with another potato plant.

In another aspect, the present invention provides for Single Gene Converted plants of FL 2048. The single gene transferred may be a dominant or recessive allele. Preferably, the single gene transferred will confer such traits as herbicide resistance, insect resistance, resistance for bacterial, fungal or viral disease, uniformity and increase in concentration of starch and other carbohydrates, decrease in tendency of tuber to bruise and decrease in the rate of conversion of starch to sugars. The single gene transferred may be a naturally occurring gene or a transgene introduced through genetic engineering techniques.

DEFINITIONS

In the description and tables which follow, a number of terms are used. In order to provide a clear and consistent understanding of the specification and claims, including the scope to be given such terms, the following definitions are provided:

FL Solids. Percentage of solid matter contained in tubers. FL Solids=(178.093×Specific Gravity)−175.560.

Solid/Acre. Marketable yield (in pounds)×FL Solids.

Total Yield. Total weight of all harvested tubers.

Marketable Yield. Weight of all tubers harvested that are between 2 and 4 inches in diameter; Measured in cwt (hundred weight) cwt=100 pounds Vine Maturity. Plants ability to continue to utilize carbohydrates and photosynthesize. Scale of 1 to 5.1=dead vines 5=vines green, still flowering.

DETAILED DESCRIPTION OF THE INVENTION

A novel potato cultivar of the present invention, which has been designated FL 2048, has been obtained by selectively crossbreeding parental clones through several generations. These parents were selected as breeding parents because of their high yields, excellent chip color off the field and out of storage, and resistance to Golden Nematode.

FL 2048 is a late season chipping variety with white fleshed and round to oblong tubers. FL 2048 has outstanding attributes that contribute to excellent chip appearance, and good flavor.

The chip appearance, manufacturing efficiency and consumer acceptability have been equal or superior to checks.

FL 2048 has been uniform and stable since its origin as a single plant in 1997. No variants of FL 2048 have been observed.

In addition to the morphological characteristics and disease and pest resistance as described above, the plants of this invention are characterized by their protein "fingerprint" patterns. The protein "fingerprint" is determined by separating tuber proteins on an electrophoretic gel under certain defined conditions. The pattern of the proteins, attributable to their differential mobilities on the electrophoretic gel, have been found to be characteristic of the particular plant involved. This pattern has thus been termed a "fingerprint." Isozyme fingerprints of all available North American potato varieties have revealed that no two varieties have the same pattern for the enzymes tested. (Douches and Ludlam, 1991). The isozyme fingerprint of FL 2048 has been established as distinct from that of any other variety tested, including Atlantic (Douches and Ludlam, 1991). These techniques generally involve extracting proteins from the tuber and separating them electrophoretically.

Potato variety FL 2048 has the following morphologic and other characteristics.

VARIETY DESCRIPTION INFORMATION

Classification: *Solanum Tuberosum* L.
Plant characteristics: (Observed at beginning of bloom)
Growth habit: Erect (45° with ground)
Type: Intermediate
Maturity: 121–124 days after planting (DAP) at vine senescence
Planting Date: Jun. 3, 2003
Region Area: Rhinelander, Wis.
Maturity Class: Late (121–130 DAP)
Stem Characteristics: (Observed at Early First Bloom)
Stem (anthocyanin coloration): Weak
Stem (wings): Strong
Leaf Characteristics: (Observed Fully Developed Leaves Located in the Middle One-Third of Plant):
Leaf (color): Medium green, RHS 147A
Leaf (pubescence density): Medium
Leaf (pubescence length): Medium
Leaf (silhouette): Medium-Open
Leaf stipules (size): Medium
Petioles (anthocyanin coloration): Very weak
Terminal leaflet (shape): Narrowly ovate
Terminal leaflet (shape of tip): Acuminate
Terminal leaflet (shape of base): Truncate
Terminal leaflet (margin waviness): Weak
Primary leaflets (average pairs): 5
Primary leaflets (shape of tip): Cuspidate
Primary leaflets (size): Large
Primary leaflets (shape): Narrowly ovate
Primary leaflets (shape of base): Cordate
Number of leaflets (secondary and tertiary): 8.9
Inflorescence Characteristics:
Number of inflorescence/plant: 5.2
Number of florets/inflorescence: 15.7
Corolla (shape): Rotate
Corolla (inner surface color): White, RHS 157A
Corolla (outer surface color): White, RHS 157D
Calyx (anthocyanin coloration): Absent
Anthers (color): Yellow/Orange, RHS 14A
Anthers (shape): Narrow cone
Pollen (production): Abundant
Stigma (shape): Capitate
Stigma (color): Green, RHS 137A
Berry (production): Heavy
Tuber Characteristics:
Skin (predominant color): Buff, RHS 161C
Skin (secondary color): Absent
Skin (texture): Rough
Tuber (shape): Oval/oblong
Tuber (thickness): Medium thick
Tuber length (mm): 74.6
Tuber width (mm): 64.4
Tuber thickness (mm): 50.0

Tuber eyes (depth): Shallow
Tuber eyes (lateral): Shallow
Tuber eyes (number): 7.25
Tuber eyes (distribution): Predominantly apical
Tuber (primary flesh color): Greyed yellow, RHS 158C
Tuber (prominence of eyebrows): Medium prominence
Secondary Tuber Flesh: Absent
Number of Tubers per Plant: Low (<8)
   Disease Reactions:
Late Blight: Resistant
Powdery Scab: Moderately susceptible
Pink Rot Resistant
   Pest Reactions:
Golden Nematode: Resistant Persons of ordinary skill in the art will recognize that when the term potato plant is used in the context of the present invention, this also includes derivative varieties that retain the essential distinguishing characteristics of FL 2048, such as a Single Gene Converted plant of that variety or a transgenic derivative having one or more value-added genes incorporated therein (such as herbicide or pest resistance. Backcrossing methods can be used with the present invention to improve or introduce a characteristic into the variety. The term backcrossing as used herein refers to the repeated crossing of a hybrid progeny back to the recurrent parents. The parental potato plant which contributes the gene for the desired characteristic is termed the nonrecurrent or donor parent. This terminology refers to the fact that the nonrecurrent parent is used one time in the backcross protocol and therefore does not recur. The parental potato plant to which the gene or genes from the nonrecurrent parent are transferred is known as the recurrent parent as it is used for several rounds in the backcrossing protocol. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a potato plant is obtained wherein essentially all of the desired morphological and physiological characteristics of the recurrent parent are recovered in the converted plant, in addition to the single gene transferred from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified, substituted or supplemented with the desired gene from the nonrecurrent parent, while retaining essentially all of the rest of the desired genes, and therefore the desired physiological and morphological constitution of the original variety. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred.

Likewise, transgenes can be introduced into the plant using any of a variety of established recombinant methods well-known to persons skilled in the art, such as: Gressel, 1985, Biotechnologically Conferring Herbicide Resistance in Crops: The Present Realities, In Molecular Form and Function of the plant Genome, L van Vloten-Doting, (ed.), Plenum Press, New York; Huttner, S. L., et al., 1992, Revising Oversight of Genetically Modified Plants. *Bio/Technology;* Klee, H., et al., 1989, Plant Gene Vectors and Genetic Transformation: Plant Transformation Systems Based on the use of *Agrobacterium tumefaciens, Cell Culture and Somatic Cell Genetics of Plants;* Koncz, C., et al., 1986, The Promoter of $T_L$-DNA Gene 5 Controls the Tissue-Specific Expression of Chimeric Genes Carried by a Novel Type of *Agrobacterium* Binary Vector; *Molecular and General Genetics;* Lawson, C., et al., 1990, Engineering Resistance to Mixed Virus Infection in a Commercial Potato Cultivar: Resistance to Potato Viruses X and Potato Virus Y in Transgenic Russet Burbank, *Bio/Technology;* Mitsky, T. A., et al., 1996, Plants Resistant to Infection by PLRV. U.S. Pat. No. 5,510,253; Newell, C. A., et al., 1991, *Agrobacterium*-mediated transformation of *Solanum tuberosum* L. Cv. Russet Burbank, *Plant Cell Reports;* Perlak, F. J., et al., 1993, Genetically Improved Potatoes: Protection from Damage by Colorado Potato Beetles, *Plant Molecular Biology;* all of which are specifically incorporated herein by reference.

Many single gene traits have been identified that are not regularly selected for in the development of a new variety but that can be improved by backcrossing and genetic engineering techniques. Single gene traits may or may not be transgenic, examples of these traits include but are not limited to: herbicide resistance; resistance to bacterial, fungal or viral disease; insect resistance; uniformity or increase in concentration of starch and other carbohydrates; enhanced nutritional quality; decrease in tendency of tuber to bruise; and decrease in the rate of starch conversion to sugars. These genes are generally inherited through the nucleus. Several of these single gene traits are described in U.S. Pat. No. 5,500,365, U.S. Pat. No. 5,387,756, U.S. Pat. No. 5,789,657, U.S. Pat. No. 5,503,999, U.S. Pat. No. 5,589,612, U.S. Pat. No. 5,510,253, U.S. Pat. No. 5,304,730, U.S. Pat. No. 5,382,429, U.S. Pat. No. 5,503,999, U.S. Pat. No. 5,648,249, U.S. Pat. No. 5,312,912, U.S. Pat. No. 5,498,533, U.S. Pat. No. 5,276,268, U.S. Pat. No. 4,900,676, U.S. Pat. No. 5,633,434 and U.S. Pat. No. 4,970,168, the disclosures of which are specifically hereby incorporated by reference.

DEPOSIT INFORMATION

A tuber deposit of the Frito-Lay North America, Inc. proprietary Potato cultivar FL 2048, disclosed above and recited in the appended claims has been made with American Type Culture Collection (ATCC), 10801 University Boulevard, Manassas, Va. 20110. The date of deposit was Aug. 8, 2005. The deposit of 25 vials of tubers was taken from the same deposit maintained by Frito-Lay North America, Inc., since prior to the filing date of this application. All restrictions upon this deposit have been removed, and the deposit is intended to meet all of the reguirements of 37 C.F.R. 1.801–1.809. The ATCC Accession number is PTA-6912. The deposit will be maintained in the depository for a period of 30 years, or 5 years after the last reguest, or for the effective life of the patent, whichever is longer, and will be replaced as necessary during that period.

What is claimed is:

1. A tuber, or part of a tuber, of potato cultivar FL 2048, wherein a representative sample of tubers was deposited under ATCC Accession No. PTA-6912.

2. A potato plant, or a part thereof, produced by growing the tuber, or a part of the tuber, of claim 1.

3. Pollen of the plant of claim 2.

4. An ovule of the plant of claim 2.

5. A potato plant having all the physiological and morphological characteristics of the plant of claim 2.

6. A tissue culture of the plant of claim 2.

7. A potato plant regenerated from the tissue culture of claim 6, wherein said plant has all the physiological and morphological characteristics of the potato plant grown from potato cultivar FL 2048.

8. A method for producing a hybrid potato seed comprising crossing a first parent potato plant with a second parent potato plant and harvesting the resultant hybrid potato seed, wherein said first parent potato plant or second parent potato plant or both said first potato plant and second potato plant is the potato plant of claim 2.

9. A method for producing a hybrid potato seed comprising crossing a first parent potato plant with a second parent potato plant and harvesting the resultant hybrid potato seed, wherein said first parent potato plant or second parent potato plant is the potato plant of claim 2.

10. A method for producing a potato plant that contains in its genetic material one or more transgenes, comprising crossing the potato plant of claim 2 with either a second plant of another potato variety which contains a transgene, or a transformed potato plant of the potato cultivar FL 2048 wherein a representative sample of tubers was deposited under ATCC Accession No. PTA-6912, so that the genetic material of the progeny that result from the cross contains the transgene(s) operably linked to a regulatory element, wherein said transpene confers a trait selected from the group consisting of herbicide resistance, insect resistance, and disease resistance.

11. A method of producing an herbicide resistant potato plant comprising transforming the potato plant of claim 2 with a transgene that confers herbicide resistance.

12. An herbicide resistant potato plant produced by the method of claim 11.

13. A method of producing an insect resistant potato plant comprising transforming the potato plant of claim 2 with a transgene that confers insect resistance.

14. An insect resistant potato plant produced by the method of claim 13.

15. A method of producing a disease resistant potato plant comprising transforming the potato plant of claim 2 with a transgene that confers disease resistance.

16. A disease resistant potato plant produced by the method of claim 15.

17. A method of producing a potato plant with modified carbohydrate metabolism comprising transforming the potato plant of claim 2 with one or more transgenes encoding an enzyme selected from the group consisting of phosphofructokinase, α-amylase, and ADP-glucose pyrophosphorylase, or with a transgene encoding an antisense of α-amylase mRNA.

18. A potato plant with modified carbohydrate metabolism produced by the method of claim 17.

* * * * *